United States Patent
Vokey et al.

(10) Patent No.: US 9,695,593 B2
(45) Date of Patent: Jul. 4, 2017

(54) LEAK DETECTION IN ROOF MEMBRANES

(71) Applicant: Detec Systems LLC, Bellingham, WA (US)

(72) Inventors: David E. Vokey, Sidney (CA); Mark K. Bridges, Hickory, NC (US)

(73) Assignee: Detec Systems LLC, Bellingham, WA (US)

( * ) Notice: Subject to any disclaimer, the term of this patent is extended or adjusted under 35 U.S.C. 154(b) by 84 days.

(21) Appl. No.: 14/937,507

(22) Filed: Nov. 10, 2015

(65) Prior Publication Data

US 2017/0130459 A1     May 11, 2017

(51) Int. Cl.
    *G01N 27/04*     (2006.01)
    *E04D 13/00*     (2006.01)
    *G01M 3/16*     (2006.01)

(52) U.S. Cl.
    CPC .......... *E04D 13/006* (2013.01); *G01M 3/165* (2013.01); *G01N 27/048* (2013.01)

(58) Field of Classification Search
    CPC ...... G01N 27/048; G01M 3/04; G01M 3/042; G01M 3/045; E04D 13/006
    USPC ........................................................ 324/694
    See application file for complete search history.

(56) References Cited

U.S. PATENT DOCUMENTS

| 5,081,422 A * | 1/1992 | Shih ...................... E04D 13/006 324/693 |
| 7,652,481 B2 | 1/2010 | Vokey |
| 7,872,479 B2 * | 1/2011 | Lorenz .................... G01M 3/16 324/525 |
| 8,319,508 B2 | 11/2012 | Vokey |
| 8,566,051 B2 | 10/2013 | Gunness |
| 2012/0313652 A1 * | 12/2012 | Jaman .................. G01N 27/048 324/694 |

FOREIGN PATENT DOCUMENTS

DE           3701130 A1 *    7/1988   ........... E04D 13/006

* cited by examiner

*Primary Examiner* — Walter L Lindsay, Jr.
*Assistant Examiner* — Milton Gonzalez
(74) *Attorney, Agent, or Firm* — Adrian D. Battison; Ade & Company Inc.

(57) ABSTRACT

Leaks in a roof membrane are detected by applying a grid of electrically conductive shielding elements on the upper surface separating the membrane into a plurality of zones and generating a potential difference between the elements and a conductive component such as the roof deck or a layer at the deck. In each zone a respective one of a plurality of sensor conductors is mounted separate from the shielding elements and an electrical potential difference is applied between the sensor and the conductive component such that, in the presence of a leak located within the zone, current flows between the sensor conductor and the conductive component through moisture at the leak for detection of the current or resistance indicative of a leak.

16 Claims, 5 Drawing Sheets

LEAK DETECTION IN ROOF MEMBRANES

The present invention relates to a system for monitoring roof membranes for the presence and location of moisture penetration. It has particular application to monitoring low-slope and flat roofs of residential and commercial buildings for undesired water ingress.

BACKGROUND OF THE INVENTION

The failure to detect, find and correct minor roof deterioration in the earliest stages is considered the greatest cause of premature roof failure. This is particularly true of roofing materials applied on low-slope or flat roofs. Costly roofing problems are often the result of design deficiencies or faulty application of the roof system. Even when properly designed and applied, all roofing materials deteriorate from exposure to the weather at rates determined largely by the kind of material and the conditions of exposure.

Several methods have been used to try and locate roof leaks after they have occurred. This is becomes a particular problem for inverted roof assembly membranes (IRMA) roofs where the roof membrane is typically bonded to a concrete deck and any leak detection system needs to be located on top of the membrane which is usually covered with a thin layer of water. The detection system must then locate any membrane breach through the water layer to the deck below while avoiding other paths to ground formed by roof drain, pipe penetrations, and metal flashings.

Electric field vector mapping uses a wire loop around the perimeter of the roof surface to introduce an electric potential between the structural deck and a selected roof area which is sprayed with water. The electric field potential caused by a conductive path to any roof membrane damage is then located using a sensitive voltmeter and a pair of probes. The vector mapping method it limited in its ability to locate the ground fault signal when the IRMA roof includes insulation and heavy overburden such as a vegetative covering.

A roof leak monitoring system is detailed in U.S. Pat. No. 7,652,481 (Vokey) issued Jan. 26, 2010 to Detec Systems LLC discloses an arrangement for leak detection on flat roof systems using a gridded system of wire sensors whereby the X and Y wires that form a grid are alternately operated as an electric guard and then as a leak detection sensor measuring the conductivity to ground at a membrane breach through the water on the surface of the membrane. The method relies on the assumption that a breach through the membrane will be located coincidentally at an intersection of the x and y wires of the common grid section. However, where there are two breaches including a first breach close to an x grid location only and a second breach at a location next to a y grid location only can, the analysis of the voltages can result in an incorrect assessment that there is a single breach in the grid sections where the x and y wires of the grid intersect.

An improvement to this arrangement is also shown in U.S. Pat. No. 8,319,508 (Vokey) issued Nov. 27, 2012.

A yet further improvement is shown in Published US application 2014/0361796 which shows that, where a roof deck is used which has no or low electrical conductivity, a measurement system can be provided where the current is detected between a sensor on top of the membrane and a conductive layer underneath the membrane connecting the deck to the membrane such as an adhesive.

The disclosure of the above Vokey patents is incorporated herein by reference or may be referred to for further details of the subject matter claimed herein.

A more recent roof leak monitoring system is detailed in U.S. Pat. No. 8,566,051 issued Oct. 22, 2013, to Gunness which describes a system for detecting and locating a leak through a membrane that includes a detector array and computer. The detector array includes a boundary wire loop, sensors, and leads. The boundary wire loop surrounds the area of the membrane to be tested and generates electrical tension on the surface of the membrane. The sensors are laid out in a sensor array and are placed on top of the membrane and within the boundary wire loop. The sensors are encased in a plastic covered cable or form individual wires which have open ends for their terminations so as to define a cable so that the sensors made by the open terminations form a chain. Each sensor communicates individually with the computer and the signals from the sensors are used by the computer to perform vector mapping that detects and locates leaks through the membrane. This is an automated form of vector mapping which relies on a uniform and continuous covering of water over the membrane to locate breaches accurately.

All of the above methods are usually employed to assist in locating roof leaks on IRMA assemblies.

SUMMARY OF THE INVENTION

It is an object of the present invention to provide a method for monitoring leaks in a flat or low slope roof construction of the type having an impermeable membrane applied over an underlying horizontal support.

According to the present invention there is provided a method of detecting a leak in a roof where the roof comprises a generally horizontal roof support deck with a water impermeable membrane applied onto the upper surface of the support deck so as to define an upper surface of the membrane and a lower surface of the membrane, the method comprising:

applying electrically conductive shielding elements on the upper surface of the roof membrane in an X and Y grid pattern so as to be in electrical communication with any moisture on the upper surface;

the X and Y grid pattern of the electrically conductive shielding elements providing separation of the membrane into a plurality of zones each being bounded on two first sides by two of the electrically conductive shielding elements extending in the X direction and being bounded on two second sides by two of the electrically conductive shielding elements extending in the Y direction;

generating an electrical potential difference between the electrically conductive shielding elements on the upper surface of the membrane and a conductive component at or adjacent the roof deck on the underside of the membrane;

in each of the zones locating a respective one of a plurality of sensor conductors on the upper surface of the membrane;

each of the sensor conductors being separate from the electrically conductive shielding elements;

while the electrical potential difference is applied between the electrically conductive shielding elements and the conductive component, generating an electrical potential difference between the sensor conductor on the upper surface of the membrane and the conductive component on the underside of the membrane such that, in the presence of a leak located within the zone, current flows between the sensor conductor and the conductive component through moisture at the leak;

and detecting said current flowing between the sensor conductor and the conductive component through moisture at the leak to determine the presence of the leak.

Preferably the method includes operating switches in sequence to measure and record the current from the sensor conductor in each zone sequentially. However some or all of the sensors may be operated simultaneously.

Preferably the potential is applied to all electrically conductive shielding elements simultaneously. However the potential may be applied in zones surrounding the zone under detection with the conductors in zones in other areas of the membrane remote from the zone in detection being left unpowered.

Preferably the method includes connecting the sensor conductor in each zone to a measurement circuit and switching circuit for generating the electrical potential.

Preferably the method includes operating a switching circuit to apply the electrical potential to the electrically conductive shielding elements so that the potential is applied periodically. That is the sensing action may be repeated periodically during the life of the system to provide a continuous monitoring action over many years.

Preferably the detected current is used to provide a value of either the current flowing or the changes in resistance between the sensor and the underlying conductor for analyzing the measured resistance or current in all of the zones to identify any leaks in the membrane.

Preferably the sensor conductors are located generally at or adjacent the center of each of the zones and spaced from the electrically conductive shielding elements.

Typically the electrically conductive shielding elements and the sensor conductors are covered by a layer of aggregate or other roof build up material applied over the membrane. That is the conductor are permanently located underneath the material on the roof to provide continuous monitoring over the life of the system. The system herein is particularly advantageous where the membrane is not accessible for monitoring by other systems.

Preferably the electrical potential applied to the electrically conductive shielding elements is greater than that applied to the sensor conductors by a difference of the order of one or more volts since this acts to better shield the sensing action at the location in the zone. That is any leaks outside the zone under test are supplied with current by the shielding elements rather than by the sensor itself and thus any current drawn from the sensor is caused by leaks within the zone under test.

As a subsidiary advantage, the electrically conductive shielding elements can be used for a cathodic protection system in which a supply and switch is provided such that in the off state, when no measurements are being made, a low voltage cathodic protection supply is applied between all the electrically conductive shielding elements and the conductive component.

In some cases where necessary due to the geometry and arrangement of the roof structure, a permanent guard wire is placed around conductive roof penetrations to provide further isolation and avoid false readings.

In some cases the conductive component comprises the roof deck itself where the deck is formed of a material which is sufficiently conductive. As an alternative, the conductive component can comprise a conductive layer between the membrane and the roof deck where the roof deck is formed of a non-conductive material.

Preferably the electrically conductive shielding elements and the sensor conductors are bare wires applied by an adhesive to the upper surface of the membrane so that the wires are in electrical connection with any moisture on top of the membrane.

As an alternative the electrically conductive shielding elements and the sensor conductors can comprise an exposed conductor such as a strip carried on an adhesive tape attached to the membrane.

Thus in general there is provided a method of detecting a leak in a roof where the roof comprises a generally horizontal roof support deck with a water impermeable membrane applied onto the upper surface of the support deck which may have a layer of aggregate or other roof build up material applied over the membrane, the method comprising:

Applying guard conductors acting as shielding elements on the top surface of the roof membrane in a grid pattern providing segregation of the membrane into zones bounded by the X and Y conductors which when joined together create an electrical guard for each of the zones.

Placing a sensor conductor in the center of each of the zones created and bounded by the X and Y guard conductors.

Connecting the sensor conductors in each zone to a measurement circuit and switching circuit for generating an electrical potential between two components of the circuit;

Operating a switching circuit to apply the measurement supply voltage to the X and Y guard circuits;

by operating switches in sequence to measure and record the current or resistance to the roof deck through the any breach in the membrane and analyzing the measured resistance or current in all of the isolated zones to identify any leaking areas in the membrane.

To enhance the operation of the guard conductors which are driven from the same supply that is used for the sensor conductor measurement circuit, the voltage to the measurement circuit can be reduced by a volt more thus making the guard circuit more attractive to stray currents outside of the grid zone that is currently being measured.

The same guard conductors can also be used for a cathodic protection system in which a secondary cathodic protection supply and switch is provided such that in the off state, when no measurements are being made, a low voltage (usually about −0.85 to −1.1 Vdc), cathodic protection supply is applied between all the X and Y guard conductors and the building ground connected to the rood deck to inhibit corrosion and electrolysis.

If needed, a permanent guard wire can be place around conductive roof penetrations to provide further isolation and avoid false readings.

It will be appreciated that the present invention can be used with roof systems where the roof is horizontal or generally horizontal which includes roof panels which are slightly inclined to the horizontal.

The present invention overcomes the mentioned limitation and allows for a non-ambiguous determination of the grid enclosed section where a membrane breach has occurred.

BRIEF DESCRIPTION OF THE DRAWINGS

One embodiment of the invention will now be described in conjunction with the accompanying drawings in which.

DETAILED DESCRIPTION

Figure 1:
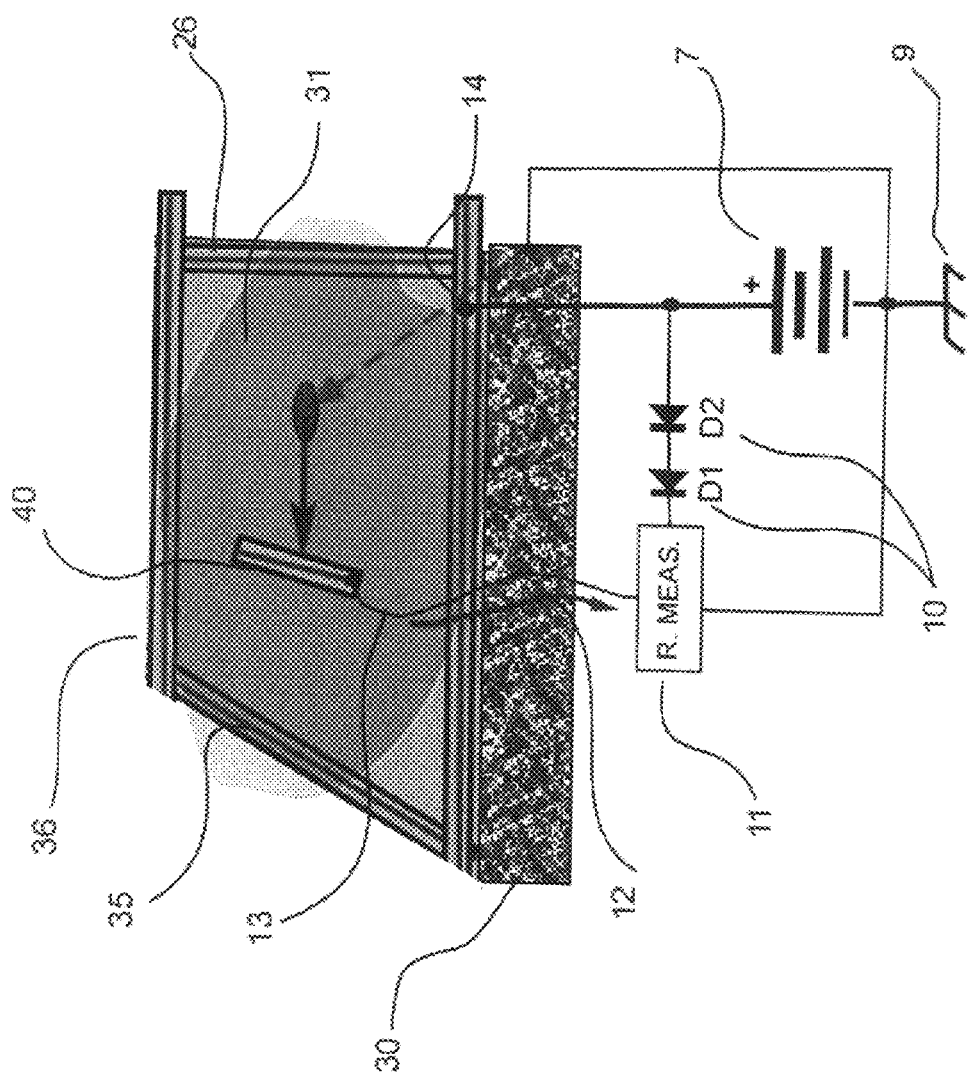
FIG. 1 is an illustration of the basic concept and circuit which details the measurement circuit and the concept of a guard circuit.
Figure 2:
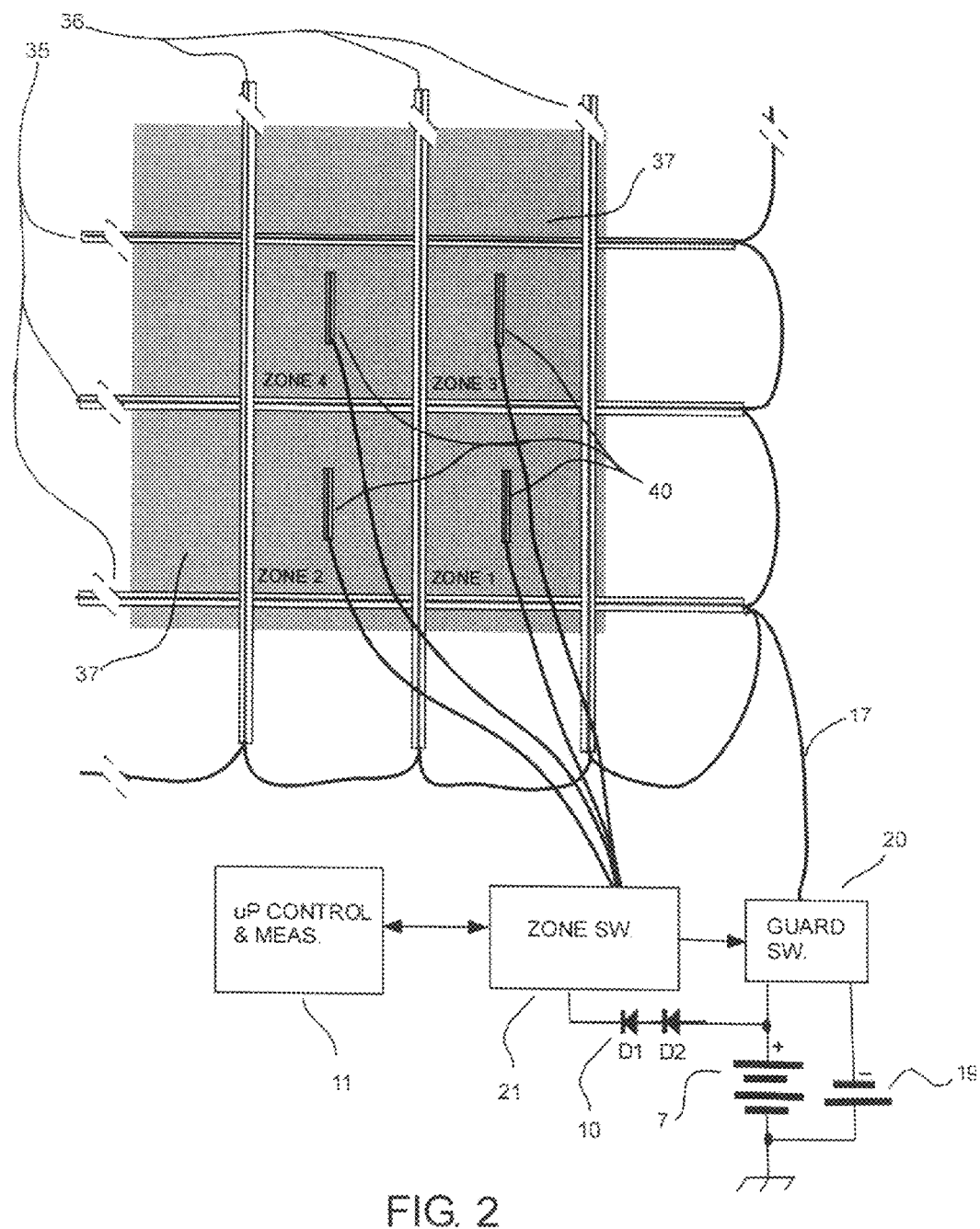
FIG. 2 is a circuit schematic showing the measuring and control circuit for multiple zones and shows the microprocessor controlled switching arrangement.

Referring now to the drawings, the overall arrangement of the subject roof membrane moisture detection system can best be seen with reference to FIGS. 1 and 2. A roof membrane 31 is illustrated which is applied as a direct covering layer over a roof deck 30. The deck is typically of concrete but can be of any suitable material that is sufficiently conductive to allow the detection of a low level electrical current travelling through the deck to a measurement ground. The membrane is a water impervious material such as thermoplastics and is sealed at any joints to provide a continuous water barrier over the roof deck. This barrier is intended to provide the leak prevention and any penetration therein caused by a puncture or faulty seal or by wear can allow the moisture to penetrate to the deck where it can cause damage or can continue into the structure to cause damage to internal structures. The membrane is typically covered by a drainage layer 2, thermal insulation 3 and a surface covering 4 such as built up roofs with gardens as shown schematically in FIG. 3.

Figure 4:
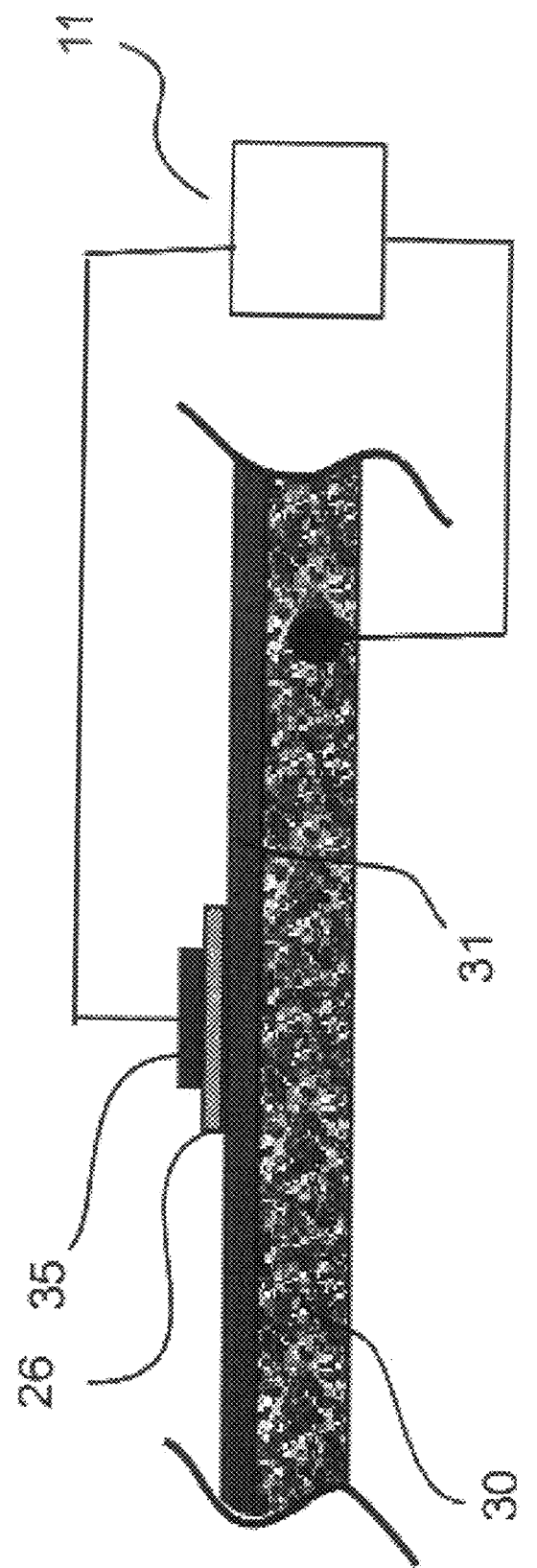
FIG. 4 is a similar view showing a modified arrangement.

Referring to FIGS. 1 and 4, copper conductors 35 and 36, illustrated as a flat conductor strip adhered to a mounting strip or tape 26, is laid across the membrane in a grid like pattern. In approximately the center of each grid a short strip of the same copper tape 40 is adhered to the membrane. This short strip of tape is the sensor that detects any current 12 that travels from a breach in the membrane 31 through a connecting cable 13 to the measurement circuit 11. The basic measurement circuit is formed by voltage source 7 with one side connected to measuring circuit 11, earth ground 9 and the conductive deck 30. The positive side the voltage source 7 is connected to the guard conductors 35 and 36, at connection 14 and to the measuring circuit 11 through dropping diodes 10. The diodes reduce the measuring voltage slightly which enhances the effectiveness of the guard conductors 35, 36.

While the potential applied between the guard conductors acting as shielding elements 35, 36 and the roof deck 30 when selected and between the guard conductors and the roof deck when not selected is typically substantially the same, advantages may be obtained by increasing the potential difference across the conductors when they are acting as shielding conductors. This can draw in more of the current from remote locations which can interfere with proper measurement at the selected measurement conductor.

FIG. 2 illustrates a larger section of a roof system with four gridded zones shown. The X and Y guard conductors 35, 36 are connecter to the guard switch 20 via cable 17. The guard switch applies the full battery potential [18] to the X and Y conductors [16] during the measurement. This forms an electrical guard isolating the zones 37 from each other. The measuring voltage is also applied to the zone switch 21 through diodes 10. The microprocessor control and measurement circuit 11 selects the zones in sequence and measures any resistance through the membrane 31 in its isolated section to ground. When all zones are measured, the results are compared to earlier readings and any degradation of the resistance in the roof deck is noted. At the end of the test cycle the guard switch connects the grid conductors 35, 36 to a low voltage cathodic protection source 19 which inhibits corrosion of the copper conductors.

Figure 3:
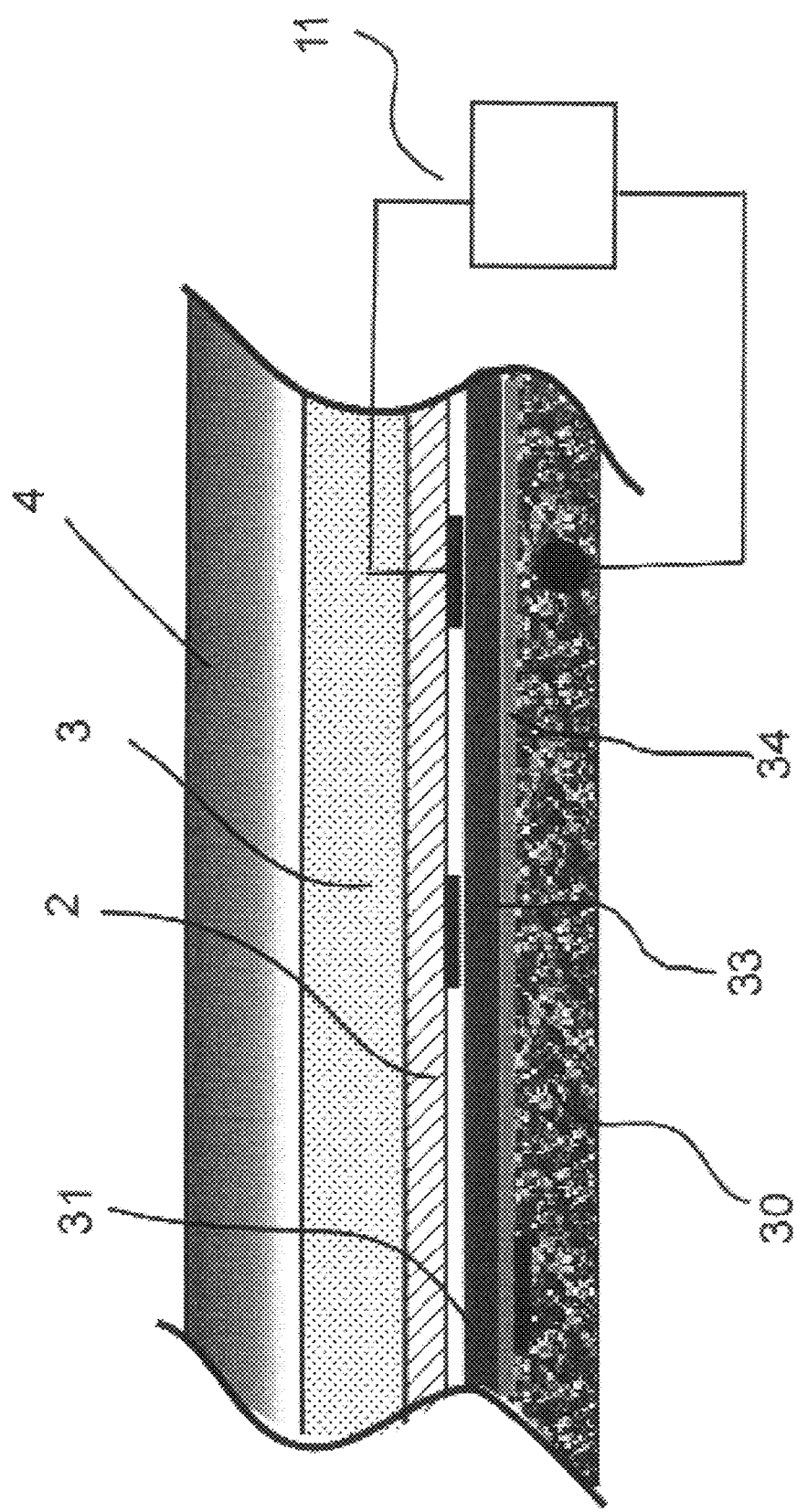
FIG. 3 is a cross-sectional view through a portion of the roof showing the arrangement of FIG. 1.

The arrangement as shown in FIG. 3 herein thus provides a method of detecting a leak in a roof with the roof comprises a generally horizontal roof support deck 30 with the membrane 31 attached over the upper surface of the deck so as to define an upper surface of the membrane and a lower surface 33 of the membrane which is attached preferably by an adhesive layer 34. The electrically conductive guard conductors or shielding elements 35 and 36 are applied in the X and Y arrangement of a grid pattern and sit directly on or adjacent the upper surface of the membrane so as to be in communication with any moisture on top of the membrane generally contained within the layers covering the membrane as shown in FIG 2. The grid pattern of the shielding elements 35, 36 provided a zone 37 bounded on two sides by the shielding elements 35 and on the other two sides by the shielding element 36.

As explained above a potential difference is generated between the shielding elements 35 and 36 on one side and the conductive component on the other side or on the side of the membrane, where the conductive component is defined either by the roof deck 30 itself as shown in FIG. 4 or by a conductive material within the adhesive layer 34 between the membrane and the deck.

Figure 5:
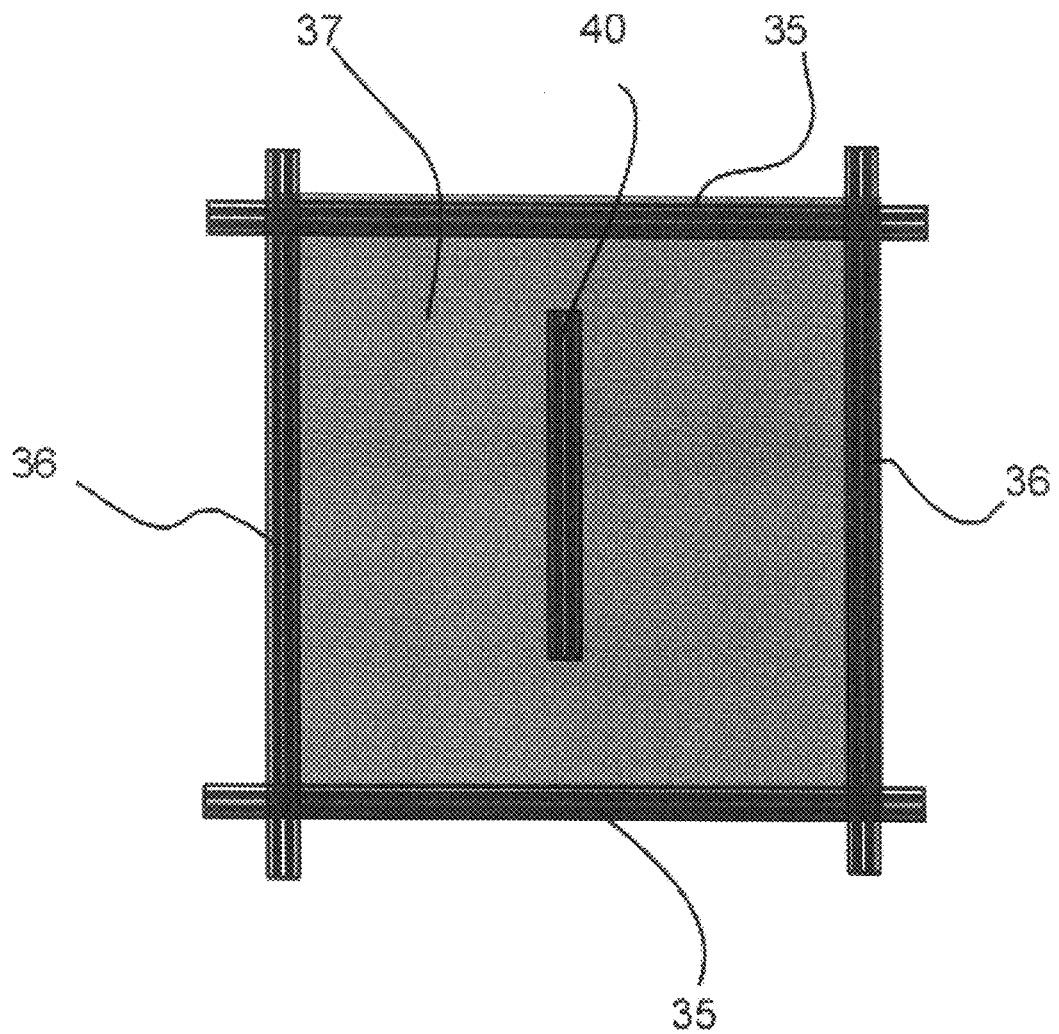
FIG. 5 is a top plan view of the arrangement FIG. 1.

As shown in FIG. 5 there is provided a short strip 40 of the conductor which is arranged out of adjacent the centre of the zone 37 and spaced from all of the surrounding conductors. The strip 40 is thus separated from the conductors and is not in electrical communication therewith.

As explained previously, while the electrical potential is applied to the conductors 35 and 36, an electrical potential is applied across the circuit defined by the strip 40 and the conductor underlying the membrane through the moisture in any leak present within the zone 37. The current in the circuit can be detected and a value provided either for the current itself or for the resistance these change due to the presence of the moisture in the leak.

The conductors 35 and 36 act so that any other leaks outside the zone 37 are not detected by the circuit through the conductor 40 since any current flowing to those leaks is provided by the conductors 35 or 36 depending upon the location of the leak.

In some cases the detection system is used to measure the current in each other zones independently and sequentially. However it is also possible that some more all of the zones may be measured simultaneously using separate sensing systems.

In the most simple system, all the conductors 35 and 36 are simultaneously connected to the potential so as to separate the whole membrane into the separate zones. However it will be appreciated that the membrane may be divided into separate areas where the detection of the leaks is carried out separately in those separate areas thus requiring only the potential to be applied to the conductors in that area.

As set out above, the conductors are 35, 36 and 40 are permanently located underneath the material on the roof so that they are protected thereby and remain in place during the life of the system. Thus the monitoring can be carried out periodically during the lifetime of the membrane so as to provide early indication of any leak, allowing early remedial action.

The conductors 40, 35 and 36 when provided in the form of a flat strip can be directly adhesively attached directly to the membrane. More conveniently the conductors can be provided in the form of a tape with the conductor carried on a band or tape of a material having a rear adhesive allowing it to be bonded easily to the membrane.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of detecting a leak in a roof where the roof comprises a generally horizontal roof support deck with a water impermeable membrane applied onto the upper surface of the roof support deck so as to define an upper surface of the membrane and a lower surface of the membrane, the method comprising:

applying electrically conductive shielding elements on the upper surface of the membrane in an X and Y grid pattern so as to be in electrical communication with any moisture on the upper surface of the membrane;

the X and Y grid pattern of the electrically conductive shielding elements providing separation of the membrane into a plurality of zones to be assessed for a leak, each zone being bounded on two first sides by two of the electrically conductive shielding elements extending in the X direction and being bounded on two second sides by two of the electrically conductive shielding elements extending in the Y direction;

generating an electrical potential difference between the electrically conductive shielding elements on the upper surface of the membrane and a conductive component at or adjacent the roof support deck on the lower surface of the membrane;

in each of the zones to be assessed for a leak, locating a respective one of a plurality of sensor conductors on the upper surface of the membrane;

each of the sensor conductors being separate from the electrically conductive shielding elements;

while the electrical potential difference is applied between the electrically conductive shielding elements and the conductive component, generating an electrical potential difference between the sensor conductor on the upper surface of the membrane and the conductive component on the underside of the membrane such that, in the presence of a leak located within the zone, current flows between the sensor conductor and the conductive component through moisture at the leak;

and detecting said current flowing between the sensor conductor and the conductive component through moisture at the leak to determine the presence of the leak.

2. The method according to claim 1, wherein operating switches in sequence to measure and record the current from the sensor conductor in each zone sequentially.

3. The method according to claim 1, wherein potential applied to all electrically conductive shielding elements simultaneously.

4. The method according to claim 1, including connecting the sensor conductor in each zone to a measurement circuit and switching circuit for generating the electrical potential.

5. The method according to claim 1, including operating a switching circuit to apply the electrical potential electrically conductive shielding elements.

6. The method according to claim 1, the detected current is used to provide a value of the current or resistance for analyzing the measured resistance or current in all of the zones to identify any leaks in the membrane.

7. The method according to claim 1, wherein the sensor conductors are located generally at or adjacent the center of each of the zones.

8. The method according to claim 1, wherein the sensor conductors an elongate conductor located in each of the zones spaced from the electrically conductive shielding elements.

9. The method according to claim 1, wherein the electrically conductive shielding elements and the sensor conductors are covered by a layer of aggregate or other roof build up material applied over the membrane.

10. The method according to claim 1, wherein the electrical potential applied to the electrically conductive shielding elements is greater than that applied to the sensor conductors.

11. The method according to claim 1, wherein the electrically conductive shielding elements are used for a cathodic protection system in which a supply and switch is provided such that in the off state, when no measurements are being made, a low voltage cathodic protection supply is applied between all the electrically conductive shielding elements and the conductive component.

12. The method according to claim 1, wherein a permanent guard wire is placed around conductive roof penetrations to provide further isolation and avoid false readings.

13. The method according to claim 1, wherein the conductive component comprises the roof support deck.

14. The method according to claim 1, wherein the conductive component comprises a conductive layer between the membrane and the roof support deck where the roof support deck is formed of a non-conductive material.

15. The method according to claim 1, wherein said electrically conductive shielding elements and the sensor conductors are bare wires applied to the upper surface of the membrane.

16. The method according to claim 1, wherein said electrically conductive shielding elements and the sensor conductors comprise an exposed conductor on an adhesive tape attached to the membrane.

* * * * *